US007842487B2

(12) United States Patent
Hollander et al.

(10) Patent No.: US 7,842,487 B2
(45) Date of Patent: Nov. 30, 2010

(54) HYARULONIC ACID DERIVATIVE BASED THREE DIMENSIONAL MATRIX

(75) Inventors: Anthony P. Hollander, Bristol (GB); Alessandria Pavesio, Padova (IT)

(73) Assignee: Fidia Advanced Biopolymers S.r.l., Abano Terme (IT)

( * ) Notice: Subject to any disclaimer, the term of this patent is extended or adjusted under 35 U.S.C. 154(b) by 988 days.

(21) Appl. No.: 10/590,250

(22) PCT Filed: Feb. 25, 2005

(86) PCT No.: PCT/EP2005/050817

§ 371 (c)(1), (2), (4) Date: Aug. 17, 2006

(87) PCT Pub. No.: WO2005/082433

PCT Pub. Date: Sep. 9, 2005

(65) Prior Publication Data
US 2008/0317808 A1    Dec. 25, 2008

(30) Foreign Application Priority Data
Feb. 27, 2004    (IT)    .............................. PD04A0053

(51) Int. Cl.
C12N 5/02 (2006.01)
C12N 11/02 (2006.01)
A61F 2/00 (2006.01)
(52) U.S. Cl. ........................ 435/177; 435/325; 435/395; 424/428; 424/93.7
(58) Field of Classification Search ................. 424/426, 424/93.7; 435/177, 395, 325
See application file for complete search history.

(56) References Cited

U.S. PATENT DOCUMENTS 6,737,072 B1 * 5/2004 Angele et al. ................ 424/426

FOREIGN PATENT DOCUMENTS

| WO | WO 00/32251 | * | 6/2000 |
| WO | WO 0037124 | | 6/2000 |
| WO | WO 02053201 | | 7/2002 |
| WO | WO 02070030 | | 9/2002 |

OTHER PUBLICATIONS

Dickinson et al., "Implantation of chondrocytes seeded on esterified hyaluronic acid scaffolds in human knees," *Tissue Engineering*, vol. 9, No. 4, Aug. 2003, p. 809. Abstract.
Grigolo et al., "Transportation of chondrocytes seeded on a hyaluronan derivative Hyaff-11 into cartilage defects in rabbits," *Biomaterials*, Elsevier Science Publishers, Sep. 2001, pp. 2417-2424.
Kafienah et al., "Inhibition of cartilage degradation," *Arthritis & Rheumatism*, vol. 48, No. 3, Mar. 2003, pp. 709-718.
Van Beuningen et al., "In vivo effects of interleukin-1 on articular cartilage," *Arthritis and Rheumatism*, vol. 34, No. 5, May 1991, pp. 606-615.
Caron et al., "Chondroprotective effect of intraarticular injections of interleukin-1 receptor antagonist in experimental osteoarthritis," *Arthritis & Rheumatism*, vol. 39 No. 9, Sep. 1996, pp. 1535-1544.
Arend et al., "Inhibition of the production and effects of interleukin-1 and tumor necrosis factor α in rheumatoid osteoarthritis," *Arthritis & Rheumatism*, vol. 38, No. 2, Feb. 1995, pp. 151-160.
Ghosh et al., "Potential mechanism of action of intra-articular hyaluronan therapy in osteoarthritis: are the effects of molecular weight dependent?" *Seminars in Arthritis and Rheumatism*, vol. 32, No. 1, Aug. 2002. pp. 10-37.
Stove et al., "Effects of hyaluronan on proteoglycan content of osteoarthritic chondrocytese in vitro," *Journal of Orthopaedic Research*, Elsevier Science Ltd., 20, 2002, pp. 551-555.
Freed et al., "Neocartilage formation in vitro and in vivo using cells cultured on synthetic biodegradable polymers," *Journal of Biomedical Materials Research*, vol. 27, 1993, pp. 11-23.
Campoccia et al., "Semisynthetic resorbable materials from hyaluronan esterification," *Biomaterials*, Elsevier Science Ltd., 19, 1998, pp. 2101-2127.
Brun et al., "Chondrocyte aggregation and reorganization into three-dimensional scaffolds," *Journal of Biomedical Materials Research*, John Wiley & Sons, Inc., 46, 1999, pp. 337-346.
Aigner et al., "Cartilage tissue engineering with novel nonwoven structured biomaterial based on hyaluronic acid benzyl ester," *Journal of Biomedical Materials Research*, John Wiley & Sons, Inc., 42, 1998, pp. 172-181.

(Continued)

*Primary Examiner*—Ruth A Davis
(74) *Attorney, Agent, or Firm*—Abelman, Frayne & Schwab

(57) ABSTRACT

Use of a biological material containing: e) a three-dimensional matrix based on a hyaluronic acid derivative and optionally f) chondrocytes and/or mesenchymal cells partially or completely differentiated towards chondrocytes for the preparation of a graft to be surgically implanted into a joint cartilage damaged by or to be protected against a degenerative and/or inflammatory pathology.

9 Claims, 5 Drawing Sheets

OTHER PUBLICATIONS

Hollander et al., "Increased damage to type II collagen in osteoarthritic articular cartilage detected by a new immunoassay," *Journal of Clinical Investigation*, vol. 93, Apr. 1994, pp. 1722-1732.

Handley et al., "Assay of proteoglycan degradation," *Methods in Enzymology*, Academic Press, Inc., 1995, vol. 248, pp. 47-58.

Kozaci et al., "Degradation of type II collagen, but not proteogylcan, correlates with matrix metalloproteinase activity in cartilage explant cultures," *Arthritis & Rheumatism*, vol. 40, No. 1, Jan. 1997, pp. 164-174.

* cited by examiner

HYARULONIC ACID DERIVATIVE BASED THREE DIMENSIONAL MATRIX

FIELD OF THE INVENTION

The present invention relates to the use of a biological material containing a three-dimensional matrix based on a hyaluronic acid derivative for the preparation of graft for the protection and repair of joint cartilage damaged by degenerative pathologies such as osteoarthritis, osteoarthrosis, rheumatoid arthritis and psoriatic arthritis.

BACKGROUND OF THE INVENTION

Osteoarthrits (OA) is a pathology that is characterised by the erosion of the joint cartilage associated with the remodelling of the subchondral bone component with the formation of osteophytes.

The main causes of said pathology are the mechanical and biochemical changes affecting the joint as a whole.

These mechanical changes may be determined by irregularities in the joint system due to a number of possible causes, such as those listed below:
Slackening of the joint capsule;
Presence of loose bone matter within the joint;
Breakage of the menisci;
Joint trauma;
Erosions and/or incrustations of the joint capsule, ligaments and/or menisci, due to aging of the cartilage;
Inflammation of the joint system.

Excessive and/or incorrect loading of the joint may trigger a chondrocyte response manifested by the synthesis of enzymes that are responsible for degradation of the cartilage.

The biochemical changes resulting from cartilage degradation translate into macrophage recruitment and, hence, inflammation involving the synovial membrane too, where an inflammatory reaction often leads to the synthesis of pro-inflammatory cytokines (such as IL-1), which spread through the synovial fluid, inciting the chondrocytes to produce pro-inflammatory cytokines too (such as IL-1, TNF, IL-6).

This super-expression of IL-1 is crucial to the pathogenesis of OA.

Indeed, IL-1 enhances the synthesis, secretion and activation of metalloproteins (MMP) by the chondrocytes, protein enzymes responsible for the degradation of the cartilage matrix, prevalently constituted by collagens and proteoglycans.

Moreover, said cytokine also proves to inhibit the proliferation of chondrocytes, suppress the production of the natural inhibitors of these metalloproteins (TIMPs), stimulate the synthesis of high levels of nitric oxide (NO) by the chondrocytes themselves, while inhibiting the synthesis of type-II collagen and aggrecan, a major component of the proteoglycans that constitute cartilage (Kafienah W. et al., Arthritis Rheum. 2003, 48:709-718).

The effect of IL-1 on joint cartilage has been amply documented by results obtained from in vivo experiments performed by infusing said interleukin into the joint, thus causing histological damage to the cartilage similar in all respects to that seen in OA (van Beuningen H. M. et al., Arthritis Rheum, 1991, 34:606-615).

All the experimental data on the OA process therefore strongly support the hypothesis that IL-1 (in particular IL-1 β), and probably TNFα too, represent the main catabolic system involved in the destruction of joint tissues and, moreover, that they may constitute an endogenous source of the molecules responsible for the aforesaid cartilage damage.

Indeed, it has been demonstrated that blocking the production and/or activation of IL-1 prevents and/or decreases destruction of the joint matrix (Caron J. P. et al., Arthritis Rheum, 1996, 39:1535-1544).

High levels of IL-1 have also been detected in the synovial fluid of patients suffering from rheumatoid arthritis (RA) and psoriatic arthritis (Arend W. P. et al., Arthritis Rheum, 1995, 38:151-160).

Hyaluronic acid (HA) is one of the main molecules constituting the cartilage matrix, but it also represents the chief non-protein component of the synovial fluid.

It is a strongly hydrophilic, viscoelastic molecule that imparts lubricating properties to the synovial fluid. For this reason, HA has been used to treat OA for over 30 years, and especially to treat the pain that accompanies the condition (Ghosh P. et al., Semin Arthritis Rheum, 2002, 32:10-37).

Various studies have provided data on the protective effect of HA in maintaining cartilage integrity during the pathological process of OA, by demonstrating how the polysaccharide lessens the disintegration of the joint tissue caused by IL-1 (Stove J. et al., Journal of Orthopaedic Research, 2002, 20:551-555).

For over a decade, the direct implantation of autologous chondrocytes into damaged cartilage tissue has been used as a technique for treating joint defects, even though new tissue engineering techniques are now becoming more commonplace, although they involve the application of tissues to cartilage that has mostly been damaged by trauma, so they are not applicable to degenerative pathologies such as OA (Freed L. E. et al., J Biomed Mater Res, 1993, 27: 11-23). U.S. Pat. No. 5,902,741 describes and claims a cartilage tissue prepared in vitro, comprising a three-dimensional matrix constituted by a biocompatible polymer (such as collagen, gelatine, PGA or synthetic polymers), in which stromal cells such as chondrocytes or fibroblasts can adhere and proliferate.

U.S. Pat. No. 5,736,372 describes and claims a three-dimensional structure for the preparation of cartilage to be subsequently implanted in vivo, constituted by a synthetic biodegradable polymer (optionally also in combination with a second, non-biodegradable polymer), wherein chondrocytes can be grown.

EP 0907721 describes and claims a substrate for the growth of cells (such as chondrocytes), formed by a sponge prevalently constituted by an HA derivative.

EP 1144459 describes and claims a composite, porous matrix composed of an HA derivative and gelatine, to be loaded with chondrocytes to form a tissue-engineered cartilage.

EP 1232203 describes and claims the preparation of a matrix constituted by chitosan to be implanted in vivo.

Numerous scientific studies have amply demonstrated that the hyaluronic acid esters are completely biocompatible, biodegradable polymer (Capoccia D. et al., Biomaterials, 1998, 19:2101-2127), that can induce and favour the adhesion, proliferation and re-differentiation of human joint chondrocytes previously expanded in vitro and then loaded onto a three-dimensional matrix formed by said derivative for the in vitro production of new cartilage containing, besides the cellular component, a new extracellular matrix (Brun P. et al., J Biomed Mater Res, 1999, 46:337-346; Aigner J. et al., J Biomed Mater Res, 1998, 42:172-181). WO 03/07873 describes and claims a porous matrix (sponge) formed mainly by plasma proteins (such as fibrin), for the adhesion and proliferation of stromal cells such as chondrocytes.

Also known is the use of HA derivatives in the form of fibres (European patent No. 0618817 B1) which, when made into a non-woven fabric, constitute a three-dimensional matrix (without a cell component) to be used in the field of dermatology; moreover, said three-dimensional structures may be loaded with mesenchymal cells and kept in vitro for as long as necessary for their proliferation and/or partial differentiation (European patent No. 0863776 B1), including differentiation into chondrocytes directed by specific trophic factors.

WO02/053201 discloses the use of a biological material containing cells supported on a three dimensional scaffold formed by a hyaluronic acid derivative and an other polymer selected from natural, synthetic or semisynthetic polymers for the preparation of grafts suitable for implantation by arthroscopic techniques.

To date, all the cartilage tissues obtained in vitro by tissue engineering techniques using biomaterials (constituted by natural, seminsynthetic or synthetic polymers) have proved to be useful only for implantation to correct cartilage lesions that are not connected with a degenerative and/or inflammatory pathology such as osteoarthritis.

Indeed, in an osteoarthritic lesion the main obstacle to implantation of a device such as those described above, lies in the high possibility/probability of inserting a tissue-engineered cartilage into a joint capsule that is rich in pro-inflammatory cytokines that would inevitably determine the onset of a slow degenerative pathology, rapidly affecting the new tissues too, with consequent slow degradation of the matrix molecules newly synthesised from the cartilage tissues introduced therein.

This hypothesis has already been verified in vitro using a scaffold constituted by PGA loaded with chondrocytes of bovine origin (Kafienah W. et al., Arthritis Rheum. 2003, 48:709-718).

SUMMARY OF THE INVENTION

The present invention consists in the use of a biological material containing:
a) a three-dimensional matrix based on a hyaluronic acid derivative and optionally
b) chondrocytes and/or mesenchymal cells partially or completely differentiated towards chondrocytes for the preparation of a graft to be surgically implanted into a joint cartilage damaged by or to be protected against a degenerative and/or inflammatory pathology, such as osteoarthritis and/or osteoarthrosis, rheumatoid arthritis and psoriatic arthritis.

More preferably when the biological material contains the aforementioned cellular components (b) said graft is an in vitro cartilage tissue to be surgically implanted in vivo inside the inflamed joint capsule in which one of said degenerative pathologies has been established with consequent degradation of the extracellular cartilage matrix.

In this case said in said in vitro cartilage tissue further comprise the extracellular matrix produced by said chondrocytes or mesenchymal cells partially or completely differentiated towards chondrocytes said extracellular matrix being both said in vitro cartilage tissue, and once in vivo surgically implanted, also inside the joint cartilage affected by one of said degenerative pathologies.

DESCRIPTION OF THE FIGURES

FIG. 1A: is a photo of a macroscopic image of the cartilage explants treated with IL-1

DETAILED DESCRIPTION OF THE INVENTION

Figure 1:
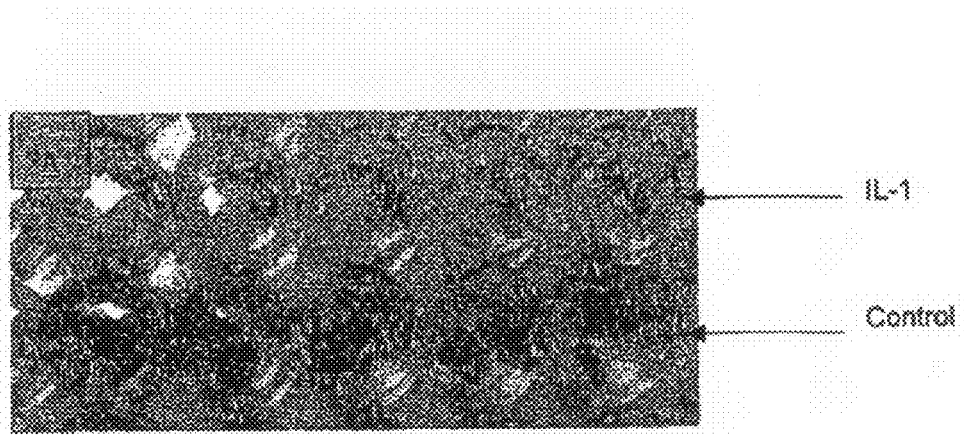
FIG. 1 B: is a photo of a macroscopic image of the tissue-engineered cartilage prepared in vitro with HYAFF®-11, after treatment with IL-1
Figure 1:
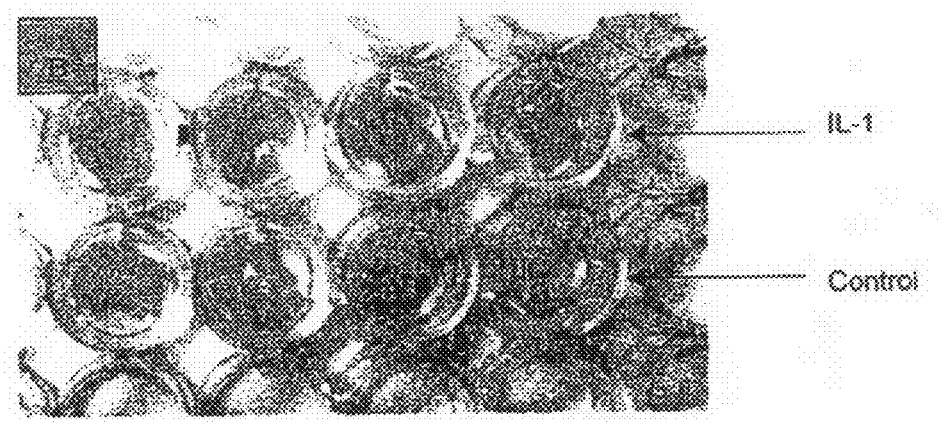

The Applicant demonstrated how the three-dimensional matrix constituted by a hyaluronic acid derivative made into a biological material and preferably loaded in vitro with autologous and/or allogenic chondrocytes, protects the new cartilage tissue that is formed both in vitro and in vivo after implantation from degradation of the molecules that form the matrix by the pro-inflammatory cytokines that stimulate the production (by the chondrocytes themselves) of proteolytic enzymes such as metalloproteins.

The present invention is therefore directed the use of the said three-dimensional matrix for the preparation of grafts to be surgically implanted into the joint cartilage as a new therapy:
in the early stages of one of said degenerative diseases and in particular osteoarthritis, at the beginning of the process of degradation of the molecules that make up the extracellular matrix of the cartilage;
in the later stages of said pathology too, when moderately and/or badly damaged areas of cartilage can be seen.

In fact the grafts when surgically implanted in the early stage of one of said degenerative disease is able to delay the degradation of proteoglycans and collagen, and, when surgically implanted in the later stage of the disease into the progressively degraded joint capsule as new, tissue-engineered cartilage, it proves able both to cover the previously created cartilage lesion and to substitute the eroded extracellular matrix with new cartilage tissue, so that the matrix will not undergo any further degradation because it is protected by hyaluronic acid derivative from the erosive action of IL-1.

HA is a hetero-polysaccharide composed of alternate residues of D-glucuronic acid and N-acetyl)lucosamine. It is a straight-chained polymer with a molecular weight that ranges between 50,000 and $13 \times 10^6$ Da, depending on the source from which it is obtained and the methods used to prepare it.

It is present in nature in the pericellular gels, in the fundamental substance of the connective tissue of vertebrate organisms (of which it is one of the main components), in the synovial fluid of the joints, in the vitreous humor and in the umbilical cord.

HA therefore plays a major role in biological organisms, especially as a mechanical support for many kinds of cells, such as those of the skin, tendons, muscles and cartilage.

Moreover, it is known that HA, by its membrane receptor CD44, modulates many divers processes relative to cell physiology and biology, such as cell proliferation, migration and differentiation and angiogenesis, and that it has other functions such as tissue hydration and joint lubrication.

The HA to be used in the present invention may come from various sources, for example, it can be obtained by extraction from rooster combs (European patent No. 0138572 B1), by fermentation (European patent No. 0716688 B1), or by technological means, and its molecular weight may range between 400 and $3 \times 10^6$ Da, in particular between $1 \times 10^5$ Da and $1 \times 10^6$ Da, and even more particularly between 200,000 and 750,000 Da.

The HA derivatives that can preferably be used to make three-dimensional matrices for the use according to the present invention, are listed below:

A) HA salified with organic and/or inorganic bases; and more preferably said base is NaOH;
B) HA esters with alcohols of the aliphatic, araliphatic, cycloaliphatic, aromatic, cyclic and heterocyclic series, with a percentage of esterification that may vary according to the type and length of the alcohol used, preferably between 50 and 100%, while the remaining percentage of unesterified HA may be salified with organic and/or inorganic bases (European patent No. 0216453 B1) more preferably with sodium hydroxide; these esters are commercially available with the name HYAFF®.
C) amides of HA with amines of the aliphatic, araliphatic, cycloaliphatic, aromatic, cyclic and heterocyclic series, with a percentage of amidation more preferably ranging between 0.1 and 50%, while the remaining percentage of HA that has not undergone amidation may be salified with organic and/or inorganic bases, more preferably with sodium hydroxide (European patent application, publication No. 1095064); these amides are commercially available with the name Hyadd™
D) O-sulphated derivatives of HA having preferably from 1 to 4-$OSO_3H$ per di-saccharide unit (European patent No. 0702699 B1);
E) inner esters of HA with a percentage of esterification that does not exceed 20%, and is more preferably between 0.05 and 10%, while the remaining percentage of non-esterified HA may be salified with organic and/or inorganic bases, more preferably with sodium hydroxide (European patent No. 0341745 B1); these esters are commercially available with the name ACP®
F) Deacetylated derivatives of HA: are obtained by the deacetylation of the N-acetyl-glucosamine group with a percentage of deacetylation preferably ranging between 0.1 and 30%, while all the carboxy groups of HA may be salified with organic and/or inorganic bases, more preferably with sodium hydroxide (European patent application No. 1313772);
G) percarboxylated derivatives of HA obtained by oxidising the primary hydroxyl of the N-acetyl-glucosamine unit with a degree of percarboxylation ranging between 0.1 and 100% and more preferably between 25 and 75%. All the carboxy groups of HA can be salified with organic and/or inorganic bases, more preferably with sodium hydroxide (European patent application No. 1339753) these products are commercially available with the name Hyoxx™.

The three-dimensional matrix to be used according to the present invention is preferably in the form of a non woven issue, a issue, microspheres, or a sponge.

According to a more preferred embodiment the three-dimensional matrix consists of a hyaluronic acid ester with benzyl alcohol having a percentage of esterification ranging from 75 to 100% and more preferably 100% esterification (HYAFF™ 11) in the form of a non woven tissue prepared as described in European Patent 0618817B1).

In order to demonstrate, with relative documentation, that HYAFF®-11 has a specific protective action towards the main components of the extracellular matrix of the cartilage, the following experiments were planned and performed:

Preparation of bovine cartilage explants and their culture as such;

Preparation of cultures of chondrocytes from bovine cartilage and their expansion in vitro;

Preparation of a three-dimensional matrix constituted by a non-woven fabric based on HYAFF®-11 loaded with bovine chondrocytes previously expanded in vitro (which represents the new tissue-engineered cartilage prepared in vitro);

Treatment with IL-1 of both the explant and said matrix (previously loaded with chondrocytes), to determine the effect of pro-inflammatory cytokine on the matrix molecules and on the synthesis of protein enzymes;

Measurement of the type-1 collagen released from both the explant and from the engineered matrix by the action of IL-1;

Measurement of the proteoglycans released by the action of IL-1 both from the explant and from the abovesaid matrix;

Measurement of the enzymatic activity of the proteases after treatment of the explant and of the engineered tissue with IL-1.

We report herein below in the following examples for illustrative but not limitative purposes the results obtained by carrying out the aforementioned experiments.

Example 1

Preparation of Explants of Bovine Cartilage and their Culture as Such

Fragments of bovine cartilage were taken from five adult animals and cut into sections measuring 25 mm×3 mm×10 mm.

The sections were then washed in phosphate buffer solution (PBS) containing the antibiotics Penicillin-G and Streptomycin and the anti-fungal agents Fungizone and Amphotericin.

The sections thus obtained were placed in culture wells in 400 l1 of DMEM culture medium containing Glutamine (2 mM), Penicillin-G (200 U/ml), Streptomycin (0.1 mg/ml) and HEPES (10 mM), without the presence of bovine foetal calf serum, in an incubator set at 37° C. with 5% $CO_2$, for a period of 4 weeks.

Example 2

Preparation of Chondrocyte Cultures from Bovine Cartilage and their Expansion in Vitro Fragments of bovine cartilage taken from 5 adult animals and cut into small sections were exposed to enzymatic digestion with hyaluronidase (1 mg/ml) at 37° C. for 15 min., and subsequently with trypsin (0.25%) at 37° C. for another 30 min. and lastly with bacterial collagenase (2 mg/ml) while continuously shaking overnight at room temperature. All the above said enzymes were prepared in DMEM containing 10% foetal calf serum (FCS).

The chondrocytes thus obtained were washed in PBS, centrifuged and re-suspended in DMEM culture medium with FCS also containing FGF (1 µl/ml). The cells thus obtained were then seeded on culture dishes to enable them to proliferate for a period of 7 days, in an incubator set at 37° C. with 5% $CO_2$.

Example 3

Preparation In Vitro of New, Tissue-Engineered Cartilage Constituted by a Non-Woven Fabric (Scaffold) Formed by Hyaff®-11 Loaded with Bovine Chondrocytes Previously Expanded In Vitro For purely descriptive, and not limitative, purposes, we report hereafter an example of the in vitro preparation of tissue-engineered cartilage.

The three-dimensional support represented by the non-woven fabric of HYAFF®-11 was first hydrated with culture medium and then loaded with $15 \times 10^6$ million chondrocytes per scaffold. Each scaffold was then placed in a culture dish (to which a thin layer of agarose (1%) had previously been made to adhere (to facilitate adhesion of said matrix and prevent it from moving about on the dish) immersed in DMEM medium containing FCS and FGF, while continuously shaking, in an incubator set at 37° C. for a period of 42 days. The trophic factor FGF was added only for the first 4 days, after which the medium was changed with fresh DMEM with FCS containing insulin (10 µl/ml) and ascorbic acid (50 µl/ml).

This medium was changed every 2-3 days. After 42 days of culture, each scaffold was divided into two and all the pieces thus obtained where transferred to culture wells for another four weeks, where they were immersed in DMEM culture medium without FCS (FCS is a metalloprotein enzyme inhibitor), containing Glutamine (2 mM), Penicillin-G (200 U/ml), Streptomycin (0.1 mg/ml) and HEPES (10 mM), further supplemented with insulin/transferrin/selenium. All the experiments with IL-1 were performed with scaffolds made as described above.

Example 4

Treatment with IL-1 of Both the Explant and the Cartilage Tissue Prepared In Vitro, to Determine the Effect of Pro Inflammatory Cytokine on the Molecules of the Matrix and on Protease Enzyme Synthesis A quantity equal to half the sections of cartilage explant and scaffolds containing bovine chondrocytes (prepared in vitro as previously described), was used for the experiment with IL-1 while the other half was not exposed to any kind of treatment as it represented the untreated control. Treatment protocol: IL-1 was added to the culture medium to make a final concentration of 3 nM. the medium was changed every 2-3 days, always at an IL-1 concentration of 3 nM. The experimental protocol provided for a treatment time with IL-1 of 2 or 4 weeks. All the medium eliminated each week was collected, divided by treatment week and stored at −20° C. for the final determinations.

Example 5

Measurement of Type-II Collagen Released by the Action of IL-1 Both from the Explant and the Engineered Matrix The culture medium of the explant and engineered matrix, collected each week of treatment with IL-1, was exposed to specific enzymatic digestion with proteinase K (1 mg/ml) at 56° C. for 15 hours, together with the residues of the explant and tissue collected at the end of the experiment.

A specific ELISA test (Hollander A. P. et al., J. Clin. Invest., 1994, 93:1722-1732) was used to measure the quantity of type II collagen present both in the culture samples collected weekly (including the non-treated controls) and to determine the collagen left inside the explant and HYAFF®-11 matrix after treatment with IL-1.

Example 6

Measurement of the Proteoglycans Released by the Action of IL-1 Both from the Explant and from the Engineered Matrix The culture medium of both the explant and the engineered matrix collected each week of treatment with IL-1, was exposed to specific enzymatic digestion with proteinase K as previously described for the determination of collagen, together with the residues of the explant and the matrix collected at the end of the experiment.

Using DBM (methylene blue), a specific dye, and a special colorimetric test, the concentrations of proteoglycans present in the analysed samples were subsequently determined (Handley C. J. et al., Methods Enzymol., 1995, 248:47-48).

Example 7

Measurement of the Enzymatic Activity of Metalloprotein Enzymes after Treatment with IL-1 of Both the Explant and the Engineered Tissue Metalloprotein enzyme activity was determined on all the culture media collected weekly both for the explants and for the engineered tissues and relative non-treated controls.

A fluorescent substrate was used to determine said enzymatic activity (7-methoxycoumarine-4-acetyl(MCA)-Pro-Leu-Gli-Leu-(3-(2,4-dinitrophenyl)-L-2,3di-amino-propionyl)(Dpa)-Ala-Arg-NH). The substrate and all the samples collected were first diluted in Tris-HCL buffer 0.1 M with a pH of 7.5, containing $CaCO_3$ 10 Mm and 0.2% (v/v) of Triton X-100.

The enzymatic activity of each sample was measured, by fluorometric reading two minutes after adding the substrate to the sample to be analysed and expressed as units/total µg of type-II collagen contained in each sample (and therefore determined both on the residue and on the culture medium) (Kozaci L. D. et al., Arthritis & Rheumatism, 1997, 40.164-174).

Results

As FIG. 1A clearly shows, the explants of bovine collagen are completely degraded after four weeks of treatment with IL-1, while the tissue-engineered cartilage constituted by HYAFF®-11 shows no macroscopic changes after four weeks of treatment (FIG. 1B).

Figure 2:
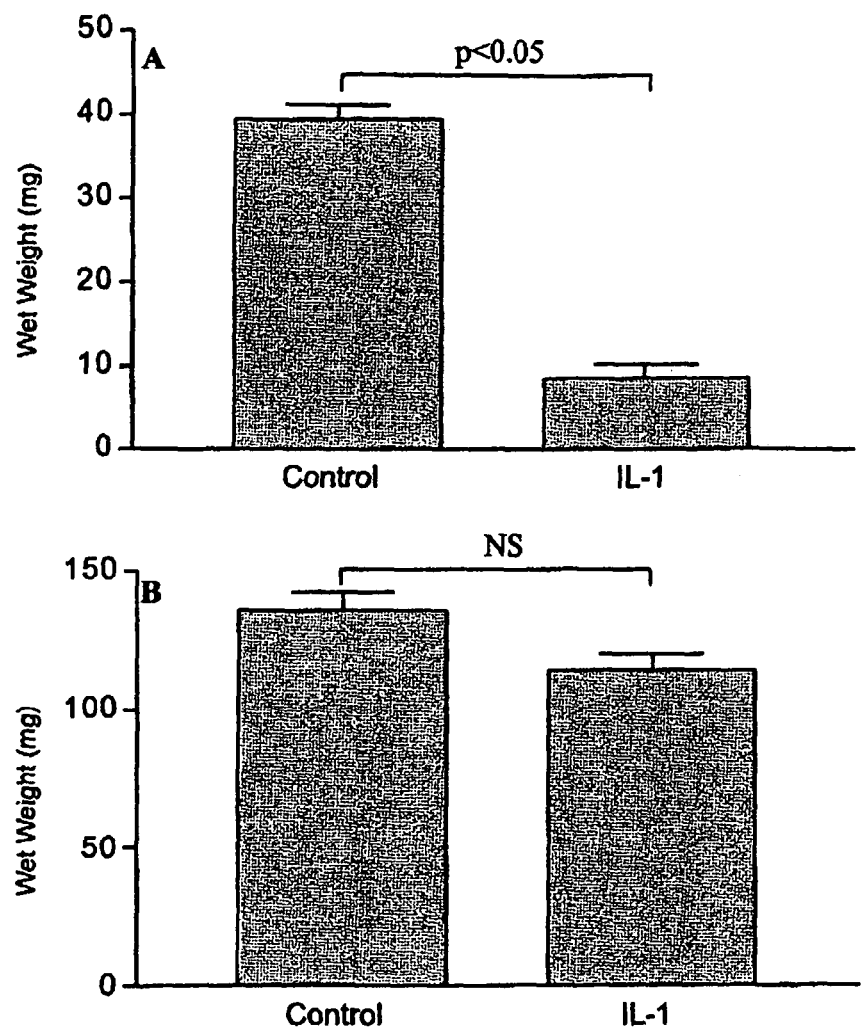
FIG. 2 represents the effect of II-1 on the wet weights (Mean±SEM; n=5) of natural cartilage (A) and tissue engineered cartilage (B). In each experiment the cartilage was exposed to 3 nM IL-1β or medium only (control) for 4 weeks. Statistical analysis was by the 2-tailed Mann-Whitney U-test.

These results are confirmed by determining the weight of the residues after treatment compared to the weight of the corresponding non-treated controls (FIG. 2 A-B).

The percentage of degradation of the proteoglycans was determined by calculating the concentration of the molecules in the culture medium for each week of treatment with IL-1 (duration of treatment: 2 weeks), and was expressed as the percentage of the total concentration of proteoglycans present both in the residue (that is, in the residue of the explant or in the residue of the engineered matrix) and in the corresponding culture medium.

Figure 3:
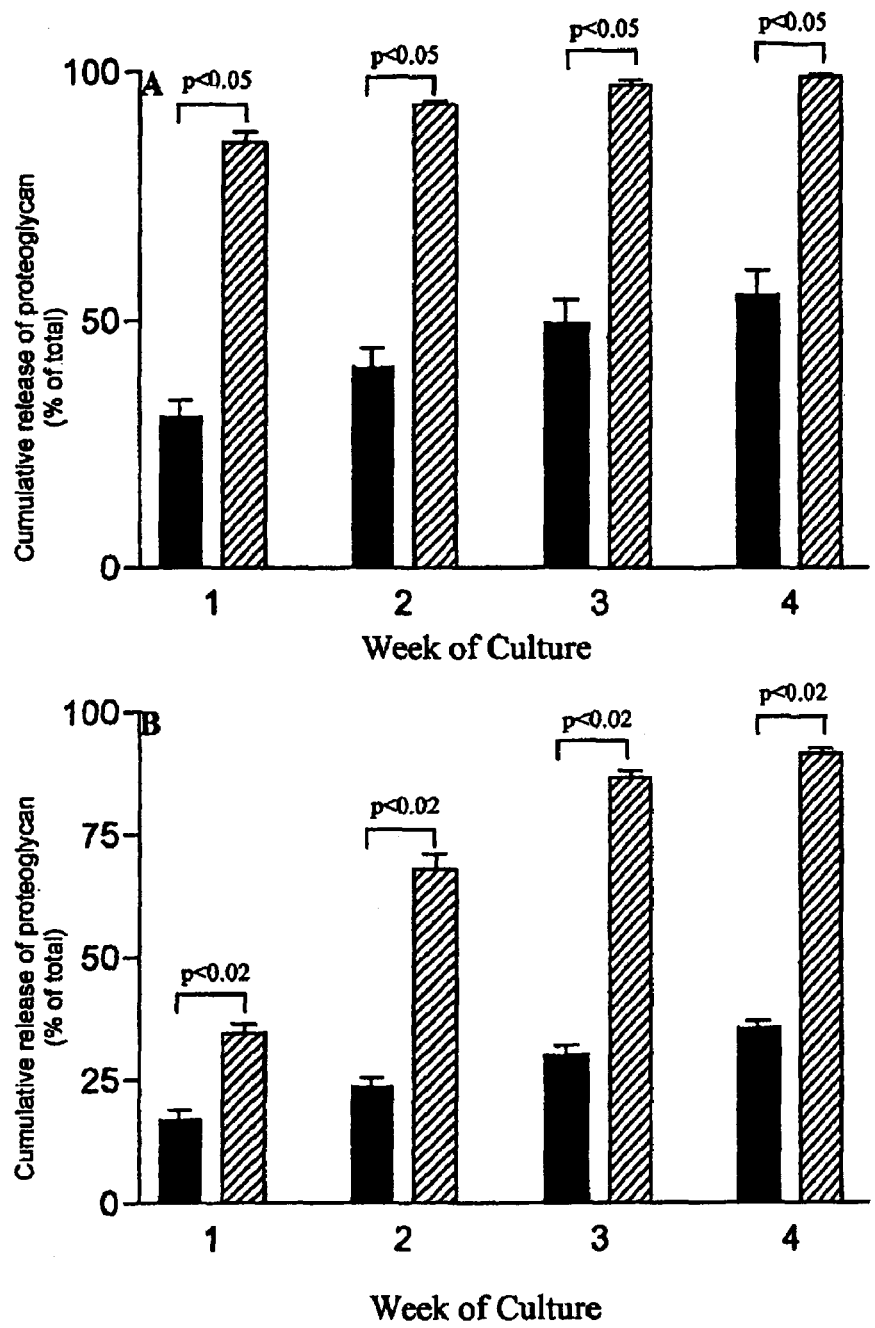
FIG. 3 represents the effect of II-1 on the proteoglycan content (Mean±SEM; n=5) of natural cartilage (A) and tissue engineered cartilage (B). In each experiment the cartilage was exposed to 3 nM IL-1 (hatched bars) or medium only (black bars) for 4 weeks. Culture medium was collected each week and residual cartilage at the end of the experiment for measurement of proteoglycan. Statistical analysis was by the 2-tailed Mann-Whitney U-test.

The results obtained show that IL-1 induces a significant degradation of the proteoglycans in the treated cartilage explants, with a percentage of degradation of 86% within the first week of treatment (FIG. 3A). IL-1 causes the degradation of proteoglycans in the engineered matrix too, but the level of degradation reaches about 70% only in the $2^{nd}$ week of treatment (FIG. 3B).

Figure 4:
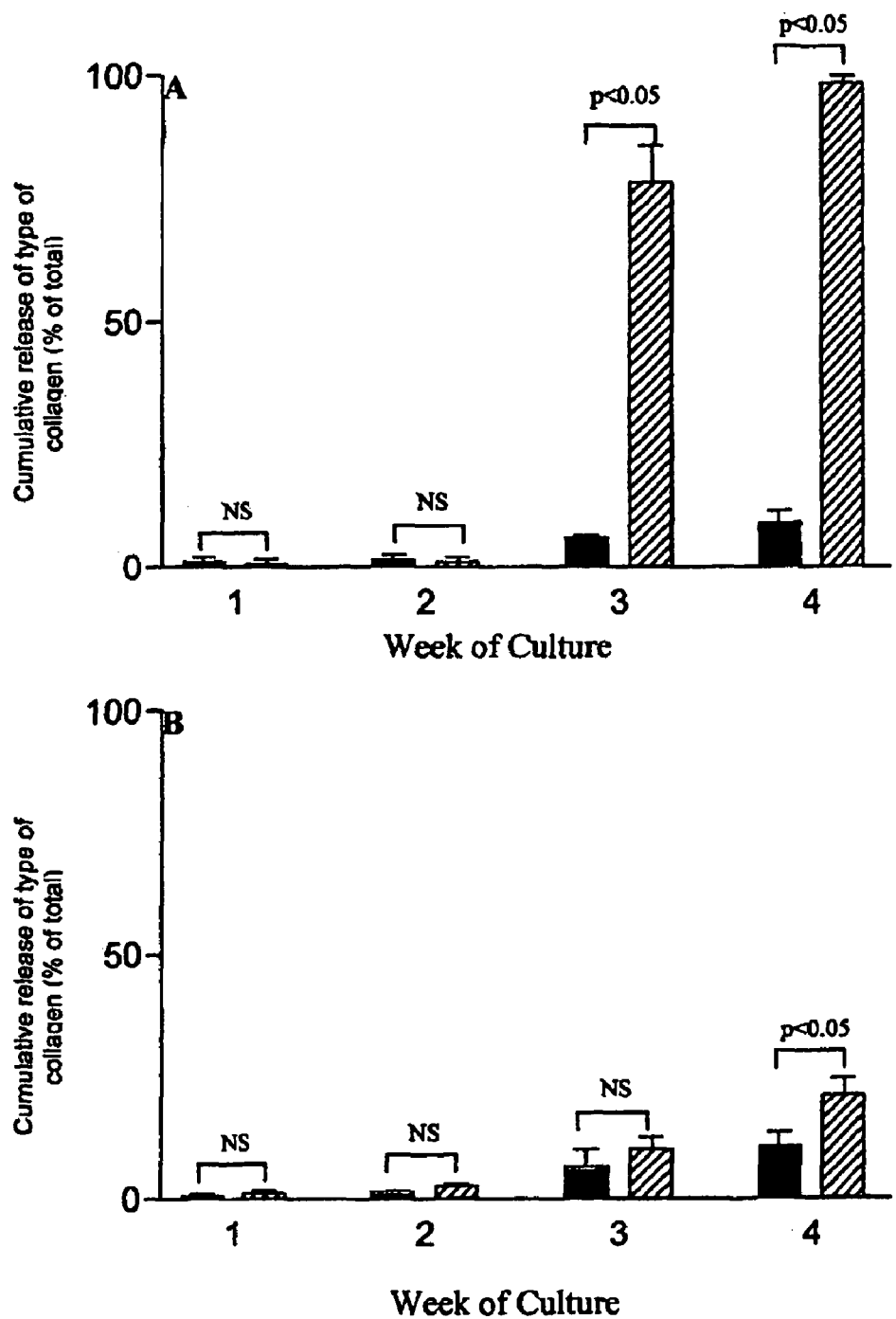
FIG. 4 reports the effect of II-1 on the type II collagen content (Mean±SEM; n=5) of natural cartilage (A) and tissue engineered cartilage (B). In each experiment the cartilage was exposed to 3 nM IL-0β (hatched bars) or medium only (black bars) for 4 weeks. Culture medium was collected each week and residual cartilage at the end of the experiment for measurement of type II collagen. Statistical analysis was by the 2-tailed Mann-Whitney U-test.

The degree of degradation of the type II collagen was determined by calculating the concentration of said protein in the culture medium for each week of treatment with IL-1 (duration of treatment 4 weeks), subsequently expressed as the percentage of total concentration of type-II collagen present both in the residue (i.e. in the residue of the explant or in the residue of the engineered matrix) and in the corresponding culture medium. The results obtained demonstrate that IL-1 in the treated cartilage explant causes the total degradation of the collagen after four weeks of treatment (FIG. 4A), while the level of degradation of the protein in the HYAFF®-11-based tissue is negligible, reaching just 20% after four weeks of treatment (FIG. 4B).

Figure 5:
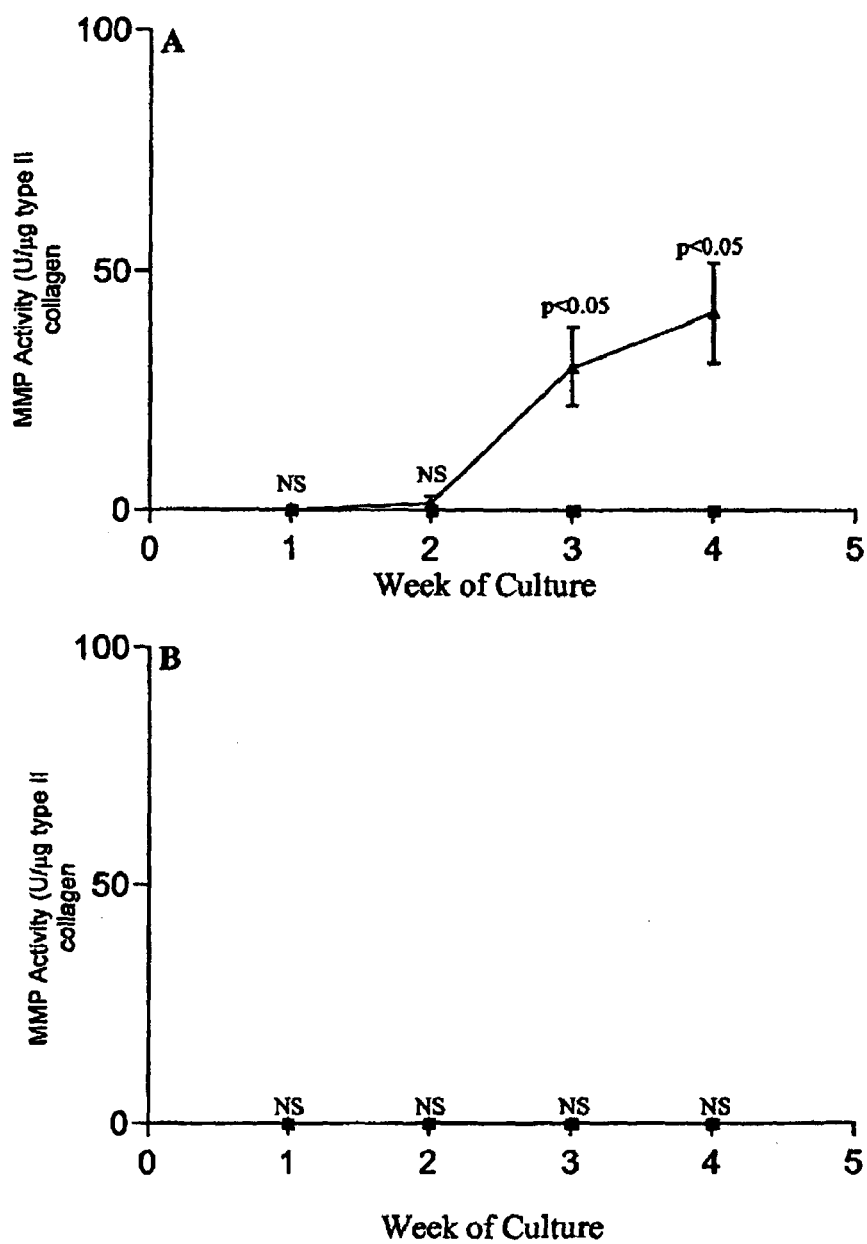
FIG. 5 reports the effect of IL-1 on the release of MMP activity (Mean±SEM; n=5) from natural cartilage (A) and tissue engineered cartilage (B). In each experiment the cartilage was exposed to 3 nM IL-1β (hatched bars) or medium only (black bars) for 4 weeks. Culture medium was collected each week and residual cartilage at the end of the experiment for measurement of MMP activity (medium) and type II collagen (medium and cartilage). Statistical analysis was by the 2-tailed Mann-Whitney U-test.

The total enzymatic activity of the metalloprotein enzymes (MMP) produced as a reaction to treatment with IL-1 both by the cartilage explant and the engineered tissue made in vitro, are quantified in FIG. 5 A-B.

IL-1 induces a strong increase in the MMP enzymes in the treated cartilage explants (after both 3 and 4 weeks of treatment) but it does not determine any increase in said enzymatic activity in the engineered tissue based on HYAFF®-11. All the above-reported results enable us to state that the biomaterial constituted by a derivative of hyaluronic acid, (and particularly by its benzyl ester HYAFF®-11), made into a three-dimensional matrix (preferably non-woven), exercises a strong protective action on the molecules that make up the extracellular cartilage matrix when this last is exposed to the erosive action of proinflammatory cytokines that have been over-produced in phlogogenic situations such as those that occur in the course of OA, rheumatoid arthritis and psoriatic arthritis.

The invention being thus described, it is clear that these methods can be modified in various ways. Such modifications are not to be considered as divergences from the spirit and purpose of the invention, but any modification that would appear to be evident to an expert in the field comes within the scope of the following claims.

The invention claimed is:

1. A surgical method for recovering or protecting a joint cartilage from a degenerative and/or inflammatory pathology, associated with the production of IL-1, selected from osteoarthritis, psoriatic and rheumatoid arthritis, said method comprising the step of implanting into a subject in need thereof a graft consisting essentially of a biological material containing:
   a) a three-dimensional matrix based on a hyaluronic acid derivative in the form of a non-woven tissue and selected from the class of hyaluronic acid benzyl esters having a percentage of esterification ranging from 75 to 100%; and optionally
   b) chondrocytes and/or mesenchymal cells partially or completely differentiated towards chondrocytes.

2. The method according to claim 1, wherein the biological material contains said cells (b), said graft being an in vitro cartilage tissue to be surgically implanted in vivo inside the joint capsule wherein the extracellular cartilage matrix is degraded by said pathology.

3. The method according to claim 2, wherein said graft further consists essentially of the extracellular matrix produced by said b) chondrocytes and/or mesenchymal cells partially or completely differentiated towards chondrocytes, said extracellular matrix being both within said graft and inside the joint cartilage after the graft implantation.

4. The method according to claim 1, wherein said graft is surgically implanted at the beginning of the process of degradation of the extracellular matrix of the cartilage.

5. The method according to claim 1, wherein said graft is surgically implanted at later stages of said pathology.

6. The method according to claim 1, wherein the average molecular weight of hyaluronic acid in the hyaluronic acid derivative range between $1 \times 10^5$ Da and $1 \times 10^6$ Da.

7. The method according to claim 6, wherein the average molecular weight of hyaluronic acid range between 200,000 and 750,000 Da.

8. The method according to claim 1, wherein the hyaluronic acid derivative has a percentage of esterification ranging from 75 to 100%, and the remaining percentage of unesterified hyaluronic acid is salified with an organic or inorganic base.

9. The method according to claim 8, wherein said base is sodium hydroxide.

* * * * *